United States Patent [19]

Adani et al.

[11] Patent Number: 5,236,353
[45] Date of Patent: Aug. 17, 1993

[54] VERTICAL COMBUSTION FURNACE

[75] Inventors: Keith J. Adani, Bridgman; Carlos Guerra, Berrien Springs, both of Mich.

[73] Assignee: Leco Corporation, St. Joseph, Mich.

[21] Appl. No.: 848,408

[22] Filed: Mar. 6, 1992

[51] Int. Cl.⁵ ............... F27B 14/00; G01N 31/12
[52] U.S. Cl. ................ 432/198; 432/241; 432/200; 432/102; 422/78
[58] Field of Search .......... 432/241, 200, 156, 102, 432/198; 422/78

[56] References Cited

U.S. PATENT DOCUMENTS

| | | | |
|---|---|---|---|
| 3,923,464 | 12/1975 | Sitek et al. | 23/253 |
| 3,958,936 | 5/1976 | Knight, Jr. | 432/156 |
| 4,282,183 | 8/1981 | Bredeweg et al. | 422/78 |
| 4,352,781 | 10/1982 | O'Brien | 422/78 |
| 4,622,009 | 11/1986 | Bredeweg | 432/156 |
| 4,805,881 | 2/1989 | Schultz et al. | 432/198 |
| 5,064,617 | 11/1991 | O'Brien et al. | 422/78 |

*Primary Examiner*—Henry C. Yuen
*Attorney, Agent, or Firm*—Price, Heneveld, Cooper, DeWitt & Litton

[57] ABSTRACT

A vertical resistive combustion furnace having a vertically oriented combustion zone in which first and second coaxially aligned tubes depend. The first tube is open at one end and closed at the other. The second tube is open at one end and partially closed at the other end and is mounted within and spaced from the first tube with the space between the coaxial tubes defining a passage for combustion products produced from a sample of material to be analyzed, disposed in said second tube. The combustion products pass upwardly in the channel through the combustion zone of the furnace so that the combustion products are hot when they exit the furnace for analysis.

17 Claims, 2 Drawing Sheets

VERTICAL COMBUSTION FURNACE

BACKGROUND OF THE INVENTION

The present invention relates to a vertical resistive combustion furnace for use in the combustion of a sample in a stream of oxygen to convert the sample into oxides of its constituent components which are then analyzed. In the case of hydrogen, for example, the hydrogen is converted to water which is analyzed.

In the past, it has been common practice to have combustion furnaces for use in the analysis of solid and liquid materials arranged with the combustion tube mounted horizontally. The input to the combustion tube was open and shielded by a stream of oxygen while the distal end of the combustion tube was closed. Many combustion tubes look like large horizontally disposed test tubes having a rounded end. An eduction tube was either inserted into the tube or provided along the outer surface of the tube and connected by a suitable glass or ceramic fitting to the combustion tube near the closed end. A sample to be analyzed was placed into a boat which was shoved into the horizontal tube. The rod used to move the sample was marked so that the laboratory technician could determine where the sample was relative to the combustion zone of the furnace. The sample could not be seen since the furnace was heavily insulated. Horizontal combustion furnaces have two significant drawbacks: 1) the sample has to be pushed in a suitable carrier to the hot zone of the furnace, and 2) the combustion tube is open to the atmosphere so the combustion products have to be pumped or drawn from the combustion tube.

In an attempt to overcome the problems associated with horizontal combustion tubes, the assignee of the present patent application launched a research effort to develop a vertical combustion furnace. This research effort resulted in the development of such a furnace which is the subject of U.S. patent application Ser. No. 659,707 entitled ANALYTICAL FURNACE which is incorporated herein by reference. The vertical combustion furnace disclosed in the aforementioned patent application is a significant improvement over horizontal combustion furnaces.

The combustion furnace employs a pair of coaxial tubes, the bottoms of which are supported and spaced by a machined stainless steel base. In assembling the furnace, the stainless steel base must be fit into the bottom of the furnace and then the outside combustion tube inserted, followed by the inside combustion tube which contains packing to support the combustion crucible in the center of the combustion zone of the furnace. The vertical furnace enables samples to be dropped through a lance into the crucible rather than being pushed. In view of the height of the base, the length of the combustion zone in the furnace is shortened. Also, the combustion products are removed through a port in the supporting base at the bottom of the furnace. While the furnace functions well, the overall construction of the furnace is relatively complex. For example, the inner combustion tube contains packing and reagent materials used to complete the combustion of the sample. These materials are put in place in the inner combustion tube after the tube is in place in the combustion furnace. Also, since an open ended tube was used to contain the packing material, it was difficult to replace the packing material in the event it became clogged.

U.S. Pat. No. 4,622,009 issued Nov. 11 1986, and assigned to the assignee of the present application discloses a vertical combustion furnace employing a U-shaped combustion tube. The sample to be combusted can be dropped into a crucible supported in one side of the tube while the reagent materials used to assure complete oxidation of the constituent elements are contained in the other leg of the U-shaped tube. While this furnace functioned for its intended purpose, it was relatively complex.

SUMMARY OF THE INVENTION

The vertical resistive combustion furnace of the present invention is a substantial improvement over the earlier combustion furnaces The furnace has an outer combustion tube and an inner combustion tube mounted coaxially and vertically in the furnace. The inner tube is spaced from the outer tube to define an annular passage for the products of combustion. The inner combustion tube is transparent and can be removed from the outer combustion tube for packing so the laboratory technician can see precisely the position of the materials and the combustion crucible in the tube before it is inserted into the furnace In the event it becomes necessary to change or clean the inner combustion tube, it can easily be lifted out of the furnace removing all of the packing material at one time. The bottom of the inner combustion tube is partially closed to provide an output port for the combustion products so that the carrier gas and combustion products can exit the bottom of the inner combustion tube and then pass upwardly through the annular passage defined by the outer wall of the inner tube and the inner wall of the outer tube. The annular passage enables the combustion products to rise vertically through the combustion zone to insure complete combustion of all the constituent materials and to heat the gaseous combustion products so that they can exit the furnace without fear of condensation, which would result in loss of material and inaccurate analysis.

DETAILED DESCRIPTION OF THE PREFERRED EMBODIMENTS

Figure 1:
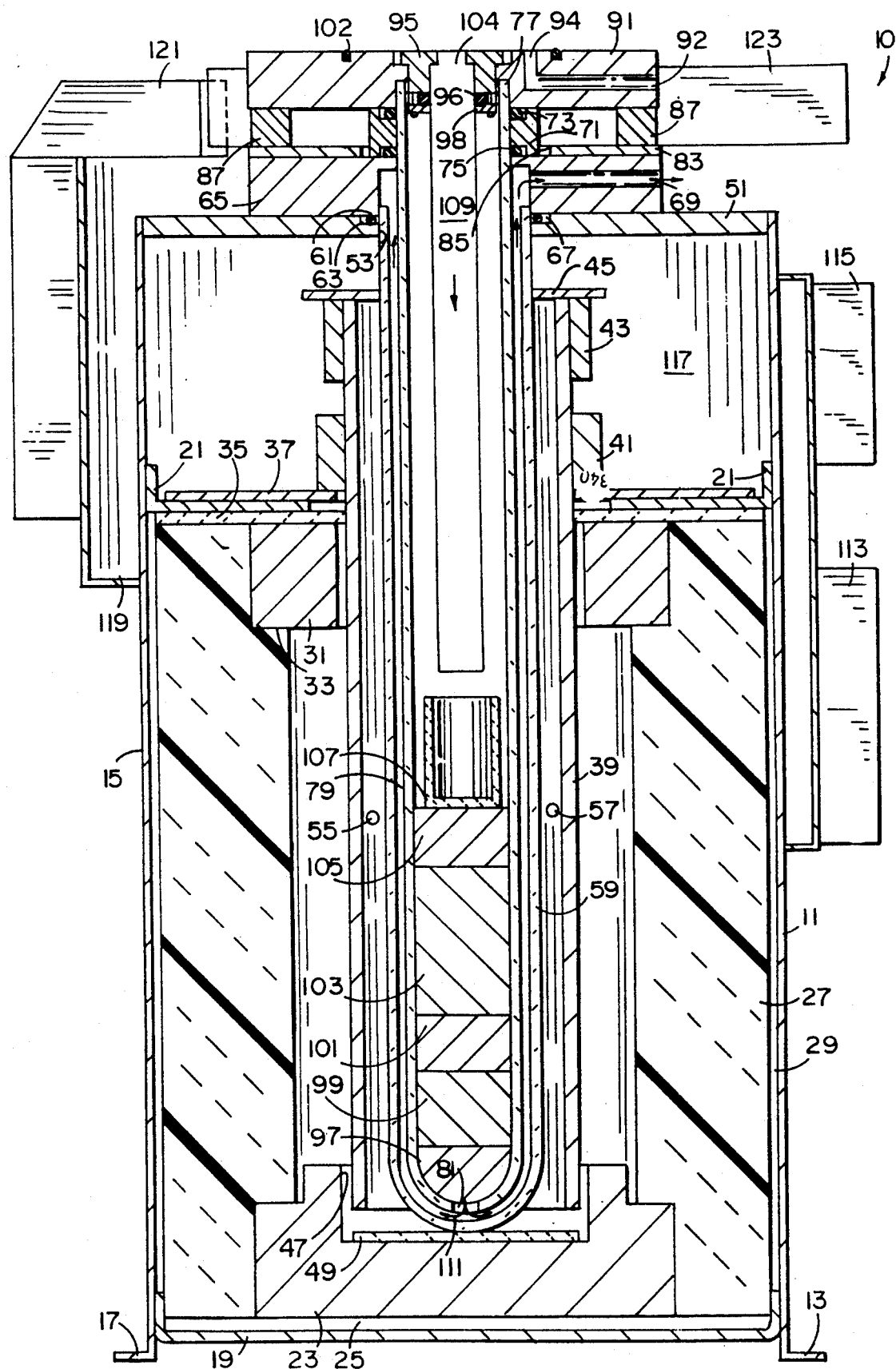
FIG. 1 is a sectional view of the combustion furnace.
Figure 2:
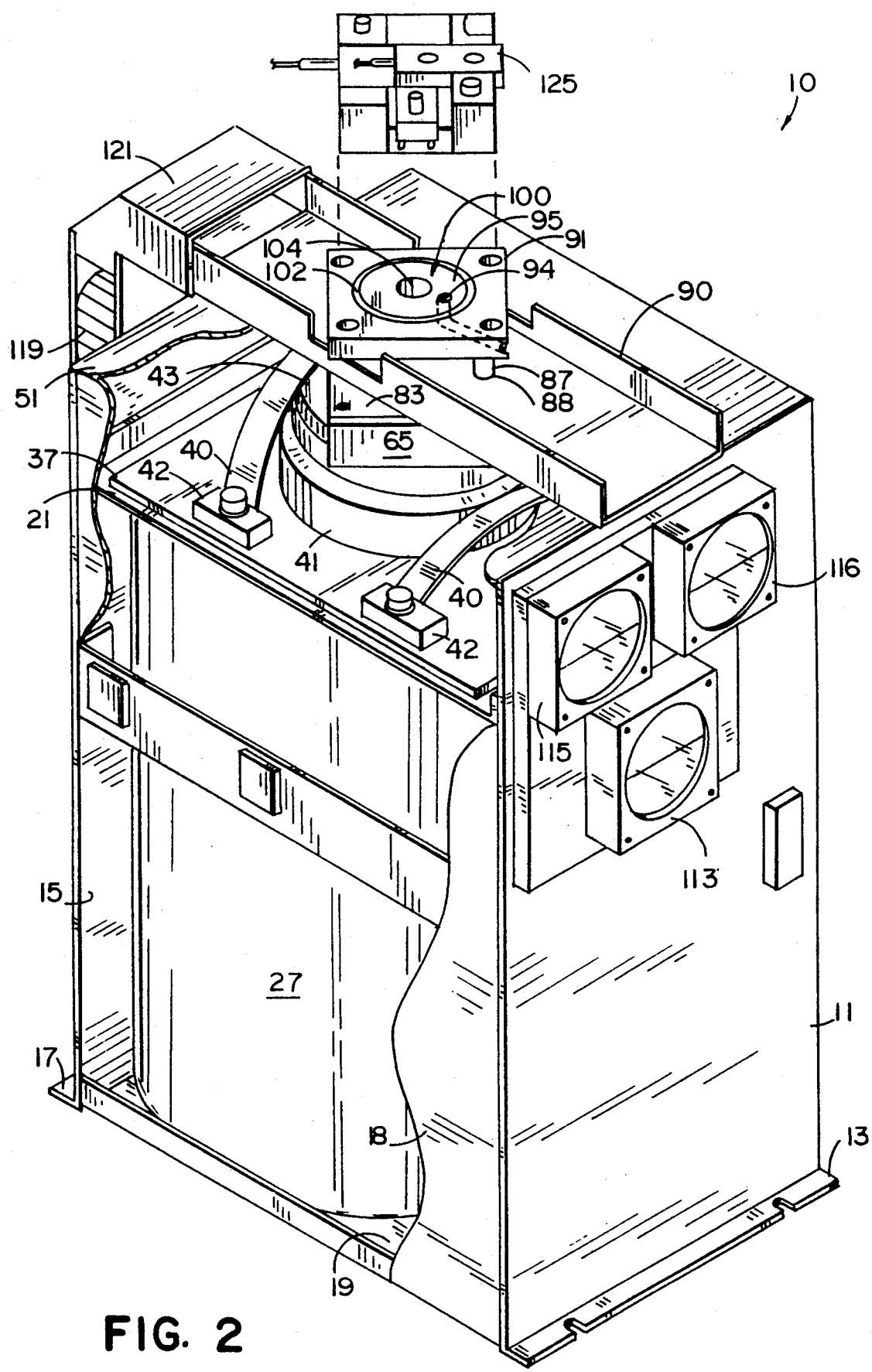
FIG. 2 is a perspective view of the combustion furnace with parts broken away to enable the interior to be seen.

Referring to FIGS. 1 and 2, the combustion furnace is indicated by the number 10. The outer configuration of the furnace is in the form of a vertical rectangular box having a front wall 11 with extending supporting foot 13, a rear wall 15 with an extending supporting foot 17 and side covers 18, only one of which is shown. A horizontal wall 19 encloses the bottom of the furnace while within the furnace a horizontally extending support wall 21 is attached to the inside surface of walls 11 and 15. A lower end cap of insulating material 23 is positioned at the bottom of the furnace and is spaced from bottom member 19 by a ceramic insulating blanket 25.

While the outer configuration of the furnace is that of a rectangular box, the furnace itself is substantially cylindrical having a thick layer of furnace insulation 27. The layer of insulation is separated from the cabinet walls by an air gap 29. An upper end cap of insulation material 31 is supported on a ledge 33 formed on furnace insulation 27. A ceramic blanket heat shield 35 is positioned on top of furnace insulation 27 and end cap 31.

A Zircar ceramic support plate 37 is supported on the top of horizontal support surface 21. The combustion furnace employs an elongated cylindrical heating element 39 which is supported by a collar of insulating material 41 on the top of Zircar plate 37. Heating element 39 is preferably a silicon carbide cylindrical heating element which is connected to a source of electrical power external to the furnace. Heavy electrical conductors 40 are connected to insulated blocks 42 on Zircar plate 37. A second clamp member 43 is attached about the silicon carbide heating element and a cover plate 45 rests on top of clamp plate 43 and the edge of heating element 39. Heating element 39 is substantially centrally positioned within the layer of insulation for the furnace and depends downwardly into a cavity 47 in lower end cap 23. A layer of Zircar material 49 is centrally positioned on the upper surface of end cap 23.

An upper mounting plate 51 is supported by walls 11 and 15 of the furnace. Upper mounting plate 51 has a centrally disposed aperture 53 therein. The combustion zone of the furnace is defined by the space between lower end cap 23 and upper cap 31. Thermocouples 55 and 57 are positioned in the combustion zone to provide an indication of the temperature therein.

The vertical combustion furnace has an outer Mullite tube 59 which is supported by an O-ring 61 on a shelf 63 on upper mounting plate 51. The distal end of the outer combustion tube 59 rests upon Zircar plate 49 supported by end cap 23. A lower loading block 65 is also supported by upper mounting plate 51. Lower loading block 65 has an internal cavity 67 therein which is sealed by O-ring 61. An exit path 69 is provided in lower loading block 65 to carry the products of combustion from inside Mullite tube 39 to the analysis equipment located outside of the combustion furnace.

A supporting ring 71 rests upon the upper surface of lower loading block 65. Support ring 71 has a pair of annular cavities therein which contain O-rings 73 and 75 which are used to support inner combustion tube 77. The inner combustion tube is made of quartz and is transparent. The combustion tube depends from O-rings 73 and 75 in support rings 71 into the combustion furnace Where it is spaced from outer combustion tube 39 by an annular passage 79. The distal end of inner combustion tube 77 has an aperture 81 through which the combustion products can flow into annular passage 79. The combustion products can then proceed upwardly through the combustion zone to the exit passage 69 in lower loading block 65. A sheet of Zircar insulation 83 is supported on the top of lower loading block 65 and has an aperture 85 therein to provide room for support ring 71. Spacers 87 are supported on the top of Zircar sheet 83 and pass through apertures 88 in air duct 90. An upper loading block 91 is supported by the spacers Upper loading block 91 has a cavity 93 therein for containing the upper portion of inner combustion tube 77.

Inner combustion tube 77 is made of quartz so it is transparent. The inner combustion tube can be loaded with various combinations of reagent materials depending on the material to be analyzed and the desired constituent products to be produced. For example, a layer of quartz wool 97 can be positioned at the bottom or distal end of the combustion tube to support a layer of furnace reagent 99 such as calcium oxide on kaolin for scrubbing out sulphur combustion products. A second layer of quartz wool 101 can be positioned above the furnace reagent which, in turn, supports a layer of tungsten oxide 103 which is used to assure complete combustion of the sample to the desired constituent gases. A third layer of quartz wool 105 is positioned on top of the tungsten oxide and supports a circular cup-shaped ceramic crucible 107 in the combustion zone of the furnace. Since the inner combustion tube 77 is made of quartz, the loading of the various layers of materials can be done outside of the furnace where the packing process can be observed by the technician. This also provides consistency of operation for the furnace since the technician can observe each layer of material being put into the inner combustion tube and can determine the amount of packing pressure, for example, to be applied to each layer.

In an embodiment of the vertical combustion furnace, the overall height of the furnace is approximately fifteen inches. A cross section of the furnace would be a square approximately nine inches on a side. The Mullite outer combustion tube is approximately thirteen and one-half inches long with a two inch outer diameter and a one and three-quarter inch inner diameter The quartz inner combustion tube is approximately fifteen inches long with a one and one-half inch outside diameter and a one and one-quarter inch inside diameter The annular passage for the combustion products is one-quarter inch in diameter. The combustion zone within the furnace is approximately seven and one-half inches long and four and one-half inches in diameter. The above numbers are representative of the sizes of the several components and are not intended, by any means, to be a limitation of the scope of the invention.

A distinct advantage of a vertical combustion furnace is that a sample can be dropped from the top of the furnace into the combustion crucible. For this purpose, a lance tube 109 is provided which is supported from upper loading block 91 and ends a short distance above combustion crucible 107. The lance is held by lance holding ring 95. An O-ring 96 is compressed by a metal ring 98 to grip the lance 109. Lance 109 can be used to drop the sample into the crucible and to provide a flow of oxygen combustion and carrier gas into crucible 107.

In the operation of the furnace, the sample would be dropped through lance 109 into crucible 107. The furnace can work with small samples and even macro samples of one gram. The sample would then be combusted in the crucible and the oxygen carrier gas, at a flow rate of approximately six liters per minute during combustion. The oxygen enters the upper loading block through port 92 and flows upwardly and exits port 94 to an annular space 100 confined between O-ring 102 on the top of upper loading block 65 and loading mechanism 125 and then flows into aperture 104 in lance holder 95. The oxygen then flows downwardly through lance 109 to crucible 107. The constituent combustion products and oxygen carrier gas flow downwardly through the several layers of furnace packing and exit through aperture 81 at the distal end of inner combustion tube 77. A directional arrow 111 is used to show the gas exiting the inner combustion tube and then passing upwardly in the annular passage surrounding the inner combustion tube up to the cavity in the lower loading block from which the gas exits through passage 69.

The preferred combustion temperature for the samples is approximately 1350° C. The combustion zone of the furnace is obviously extremely hot. In order to isolate the cabinet from this extreme heat, the previously described layers of insulation are provided about the combustion zone. Also, an air shield or space 29 is provided between the outer walls of the layers of insulation and the inner walls of the outer cabinet. A fan 113 provides a continual stream of air through space 29 to cool the cabinet. Fans 115 and 116 provide a stream of cooling air for the space 117 between Zircar plate 37 and upper mounting plate 51. A third fan 119 is connected to air ducts 121 and 90 and provides a stream of cooling air past spacers 87, and around and through cooling ring 71. While the inside of the combustion furnace is operating at approximately 1350° C., the gas exiting the furnace through passage 69 is heated to approximately 60° C. which is high enough to prevent any materials from condensing out in the furnace prior to analysis. The input portion of the furnace, that is, cover plate 95, is cooled to approximately 45° C. so that an operator could comfortably open the furnace with bare fingers to add a sample. In the preferred operation of the furnace, an automatic loading device 125 would be mounted on top of the furnace.

The furnace of the present invention is intended to operate as a closed system in contrast to the aforedescribed horizontal furnaces which were open to the atmosphere and required eduction tubes and pumps to withdraw the combustion products from the furnace. The carrier gas pressurizes the system and sweeps the combustion products from the inner combustion tube downwardly to the entry to the annular passage between the inner and outer combustion tubes and then upwardly through this passage to the lower loading block where the combustion products exit to the analysis device. A pump or other eduction means are not necessary for the operation of the furnace.

Although the invention has been described with respect to specific preferred embodiments thereof, many variations and modifications will become apparent to those skilled in the art. It is, therefore, the intention that the appended claims be interpreted as broadly as possible in view of the prior art to include all such variations and modifications.

The embodiments of the invention in which an exclusive property or privilege is claimed are defined as follows.

1. A vertical combustion furnace for converting a sample material into constituent gaseous products for analysis comprising:
   a vertically oriented combustion furnace;
   a vertical heating zone substantially centrally disposed within said combustion furnace;
   a first elongated combustion tube having an open end and a closed end, said combustion tube being vertically oriented in said vertical heating zone; and
   a second elongated combustion tube having an open end and a substantially closed other end, said second elongated combustion tube being coaxially mounted within and spaced from said first elongated combustion tube with the space between the coaxial tubes defining an annular passage for the gaseous combustion products produced in said second tube.

2. A vertical combustion furnace as set forth in claim 1, wherein said first elongated combustion tube has an internal diameter larger than the outer diameter of said second elongated combustion tube.

3. A vertical combustion furnace as set forth in claim 1, wherein said second elongated combustion tube is transparent and contains packing material visible through the wall of said second tube.

4. A vertical combustion furnace as set forth in claim 1, wherein said second elongated combustion tube has a substantially closed end defining an exit port for the products of combustion produced within said second combustion tube when a sample is combusted therein.

5. A vertical combustion furnace as set forth in claim 1, wherein said second elongated combustion tube is removably and replacably mounted in said vertically oriented first elongated combustion tube.

6. A vertical combustion furnace as set forth in claim 1, wherein said second elongated combustion tube is spaced from and suspended within said first elongated combustion tube.

7. A vertical combustion furnace as set forth in claim 1, including a loading block mounted above said second elongated combustion tube for feeding, by gravity, a sample of material to be analyzed into said second tube; and
   said loading block including an exit port for the combustion gases produced from said sample of material.

8. A vertical combustion furnace comprising:
   a cabinet for enclosing said furnace;
   a support shelf in said cabinet, said support shelf defining an aperture;
   a heating element depending from said support shelf through said aperture and being vertically aligned in said cabinet;
   a layer of insulation in said cabinet, said layer of insulation being spaced from and substantially surrounding said heating element and said cabinet and defining a combustion zone in said furnace;
   an upper mounting plate on said cabinet, said upper mounting plate defining an aperture generally aligned with the aperture in said support shelf;
   an outer combustion tube extending through said aperture in said upper mounting plate and said support shelf toward the bottom of said combustion zone in said furnace, said outer combustion tube having an open upper end and a closed bottom end near the bottom of said combustion zone; and
   an inner combustion tube coaxially aligned with and spaced from said outer combustion tube and extending toward the bottom of said outer combustion tube, said inner combustion tube having an open upper end and a partially closed bottom end near the bottom end of said outer combustion tube, the space between said coaxially mounted tubes defining a passage back through said combustion zone for the combustion products produced in said inner combustion tube.

9. A vertical combustion furnace as set forth in claim 8, including:
   a lower loading block on said upper mounting plate, said loading block defining an aperture;
   a spacer ring supported by said loading block, said upper ring defining an aperture aligned with said aperture in said loading block; and
   resilient means supported by said loading block and said spacer ring, said resilient means supporting said inner combustion tube in substantially coaxial alignment with said outer combustion tube.

10. A vertical combustion furnace as set forth in claim 9, including:
   an upper loading block supported by said spacer ring, said loading block defining an aperture therein aligned with the open end of said inner combustion tube, said loading block having a cavity therein for receiving the end portion of said inner combustion tube.

11. A vertical combustion furnace as set forth in claim 9, including:
   a cavity in the bottom surface of said lower loading block for receiving the open end portion of said outer combustion tube and the products of combustion from the passage between the spaced walls of said inner and outer combustion tubes; and
   a conduit in said lower loading block between said cavity and the outside of said lower loading block for conveying the products of combustion from said combustion furnace to apparatus for analyzing said combustion products.

12. A vertical combustion furnace as set forth in claim 10, including:
   a lance depending through said aperture in said upper loading block into the combustion zone in said furnace.

13. A vertical combustion furnace as set forth in claim 8, including:
   a cooling system for said furnace, said cooling system comprising:
   at least one fan for removing heated air from between said layer of insulation and said cabinet;
   at least one fan for removing heated air from the space in said cabinet between said support shelf and said upper mounting plate; and
   at least one fan for circulating air through said spacer ring and the space defined between said upper and lower loading blocks.

14. A vertical combustion furnace as set forth in claim 8, including gas permeable packing material in said inner combustion tube for supporting a crucible in the combustion zone in said furnace.

15. A vertical combustion furnace as set forth in claim 8, wherein said inner combustion tube is transparent.

16. A vertical combustion furnace as set forth in claim 8, wherein said inner combustion tube is quartz.

17. A vertical combustion furnace as set forth in claim 8, wherein said outer combustion tube is Mullite.

* * * * *